United States Patent [19]

Fore

[11] Patent Number: 4,838,279
[45] Date of Patent: Jun. 13, 1989

[54] RESPIRATION MONITOR

[76] Inventor: Don C. Fore, 324 N. Brown, Vinita, Okla. 74301

[21] Appl. No.: 48,896

[22] Filed: May 12, 1987

[51] Int. Cl.$^4$ ............................................... A61B 5/08
[52] U.S. Cl. ..................................... 128/721; 128/782
[58] Field of Search .................... 128/721, 782; 62/140

[56] References Cited

U.S. PATENT DOCUMENTS

| | | | |
|---|---|---|---|
| 3,120,108 | 2/1964 | Pansing | 62/140 X |
| 3,268,845 | 8/1966 | Whitmore | 128/771 X |
| 3,347,722 | 10/1967 | Kohrer | . |
| 3,414,896 | 12/1968 | Glick et al. | . |
| 3,483,861 | 12/1969 | Tiep | . |
| 3,517,999 | 1/1966 | Weaver | . |
| 3,541,442 | 11/1970 | Gaston | . |
| 3,544,986 | 12/1970 | Earling et al. | . |
| 3,658,052 | 4/1972 | Alter | . |
| 3,831,586 | 8/1974 | Petit | 338/47 |
| 3,926,177 | 12/1975 | Hardway, Jr. et al. | . |
| 4,067,005 | 1/1978 | Levy et al. | 340/279 X |
| 4,279,257 | 7/1981 | Hochstein | 128/722 |
| 4,296,757 | 10/1981 | Taylor | 128/721 |
| 4,366,821 | 1/1983 | Wittmaier et al. | 128/719 |
| 4,392,126 | 7/1983 | Loyola | 128/782 X |
| 4,433,693 | 2/1984 | Hochstein | 128/721 |
| 4,493,328 | 1/1985 | Saito | 128/782 |
| 4,664,129 | 5/1987 | Helzel et al. | 128/782 X |

FOREIGN PATENT DOCUMENTS 1570640  6/1969  France .

OTHER PUBLICATIONS

EdenTec ®, Respiration Depression, ©1987, 2 page brochure.
EdenTec ®, Continuous Cardio-Respiratory Monitoring, ©1987, 2 page brochure.
EdenTec ®, Delivers, ©1986, 3 page brochure.
Parks, Infant Heart Rate Monitor, Jun. 1983, 2 page brochure.
Briox, Model II-Infant Monitoring System, Undated, 2 page brochure.
Centurion ®-Apnea/Bradycardia/Tachycardia Detector, Calibrated For Life, Undated, 2 page brochure, price list, and letter.
Arvee Medical, Incorporated, Infant Apnea Monitor with Event Memory, Model 2400, Undated, 2 page brochure and letter.
Electronic Monitors, Inc., The RE40 Apnea/Respiration Monitor, Undated, 2 page brochure.
Electronic Monitors, Inc., HR21 Heart Rate Monitor, Undated, 2 page brochure.
Uncomplicated for Parents, Undated, 5 page brochure.
Healthdyne ®, Infant Monitor Model 16900, ©1985, rev. 1/87, 2 page brochure.
Healthdyne ®, Model 900, Infant Monitor, 02/87, ©1987, 2 page brochure and 2 page brochure, FACTS TM, 08/86.

(List continued on next page.)

Primary Examiner—William E. Wayner
Attorney, Agent, or Firm—Dunlap, Codding, Peterson & Lee

[57] ABSTRACT

A respiration monitor for monitoring respiration of an individual comprising a sending light conductor and a receiving light conductor. The sending light conductor and the receiving light conductor are held in a position generally near a portion of the individual which moves in response to the respiration motion of the individual. More particularly, the ends of the sending light conductor and the receiving light conductor are spaced a distance apart and positioned so that the distance between the end of the sending light conductor and the end of the receiving light conductor varies in response to respiration motion of the individual. A light source emits light which is received by the sending light conductor and transmitted therethrough across the distance between the ends of the sending light conductor and the receiving light conductor, such light being received by the receiving light conductor and transmitted therethrough. The light from the receiving light conductor is received and indications of respiration motion are determined in response to changes in the intensity of the light received from the receiving light conductor and output indications are provided indicative of respiration motion.

52 Claims, 6 Drawing Sheets

OTHER PUBLICATIONS

Aequitron Medical ®, Inc., Model 9200, Undated, 40 page brochure.
Puritan–Bennett Corporation, PB 223 $CO_2$ Monitor, 1987, 2 page brochure.
Puritan–Bennett Corporation, PB 254 Anesthesia Gas Monitor, Nov. 1986, 2 page brochure.
Puritan–Bennett Corporation, PB 252/253 Airway Gas Monitors, Sep. 1986, 2 page brochure.
Puritan–Bennett Corporation, PB 245 Cardiac/Airway Gas Monitor, Oct. 1986, 2 page brochure.
Puritan–Bennett Corporation, PB 251 Pulse Oximeter, Jun. 1987, 2 page brochure.
Puritan–Bennett Corporation, 222 Anesthetic Agent Monitor, Mar. 1984, 4 page brochure.

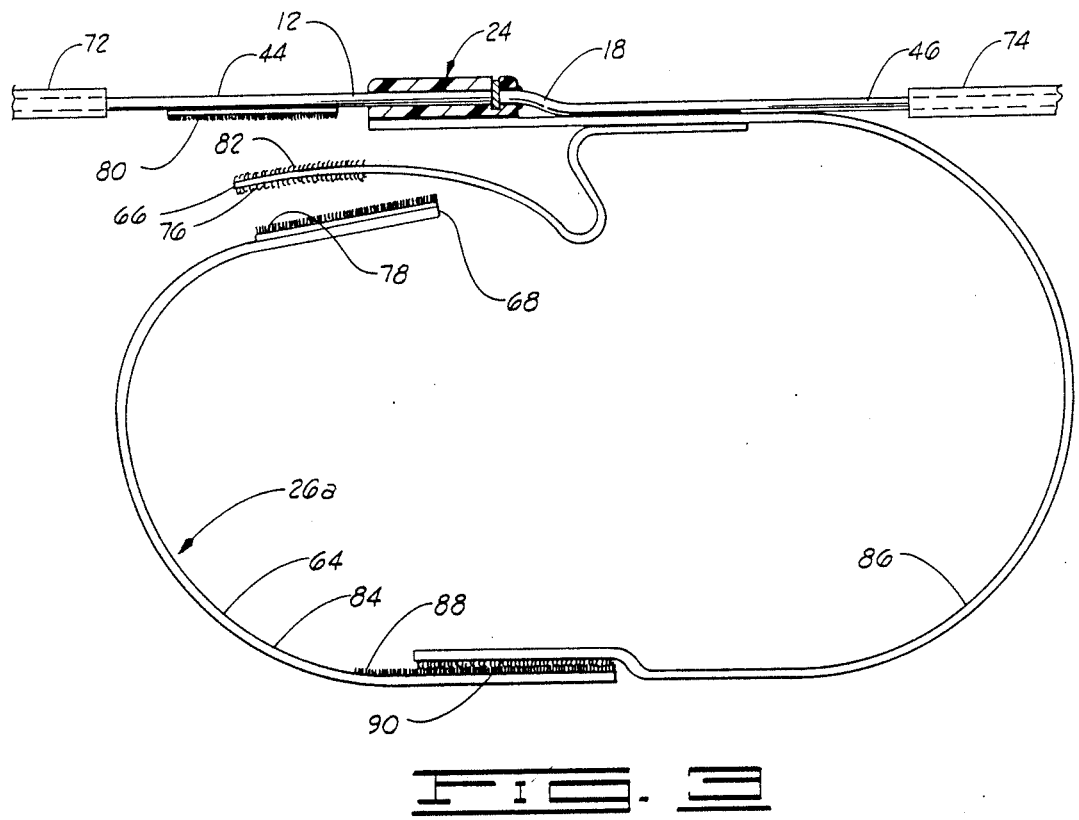
FIG. 3
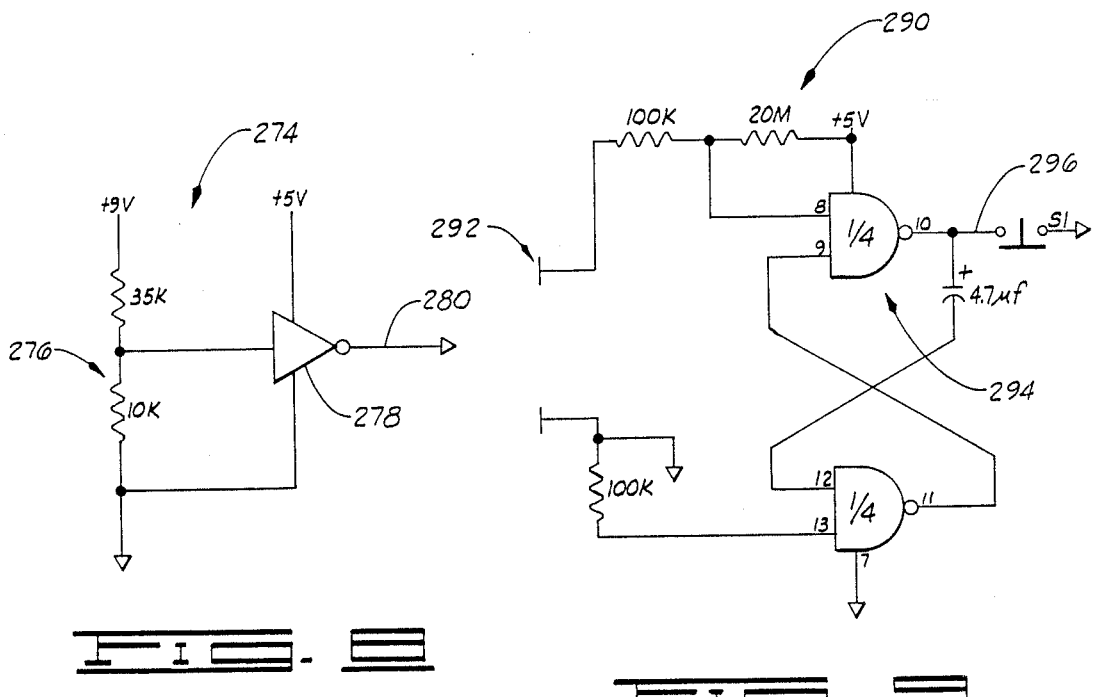
FIG. 8
FIG. 9

1

RESPIRATION MONITOR

BACKGROUND OF THE INVENTION

1. Field of the Invention

The present invention relates generally to respiration monitors and, more particularly, but not by way of limitation, to a respiration monitor having a sending and a receiving light conductor wherein the ends of the receiving and sending light conductors are spaced a distance apart which varies in response to respiration motion of an individual.

BRIEF DESCRIPTION OF THE DRAWINGS

FIG. 3 is a diagrammatic, partial elevational, partial sectional view, similar to FIG. 1, but showing a modified respiration monitor constructed in accordance with the present invention.

FIG. 6 is a schematic view of a power supply select and power failure circuit portion of the respiration monitoring control.

FIG. 8 is a schematic view of a low battery network portion of the respiration monitoring control.

FIG. 9 is a schematic view of a tampering respiration monitoring control.

DESCRIPTION OF THE PREFERRED EMBODIMENTS

Figure 1:
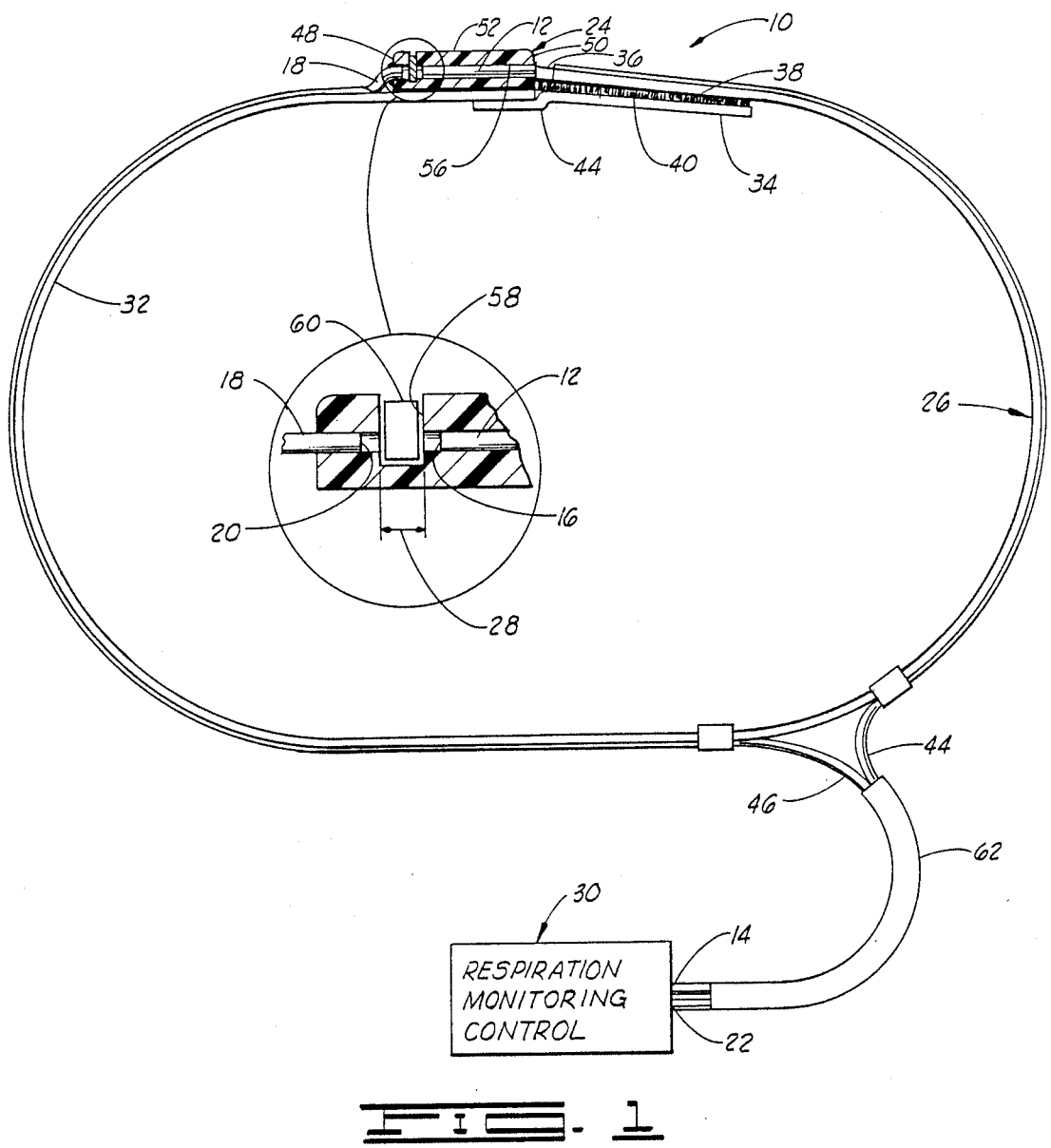
FIG. 1 is a diagrammatic, partial elevational, partial sectional view of a respiration monitor constructed in accordance with the present invention.

Shown in FIG. 1 is a diagrammatic view a respiration monitor which is constructed in accordance with the present invention and designated in FIG. 1 by the general reference numeral 10. The respiration monitor 10 includes a sending light conductor 12 having a receiving end 14 and a sending end 16, and a receiving light conductor 18 which has a receiving end 20 and a sending end 22. The sending light conductor 12 and the receiving light conductor 18 each are constructed and adapted for conducting light between the receiving and the sending ends 14 and 16 and 20 and 22, respectively, and the sending and receiving light conductors 12 and 18 more particularly are fiber optics with a plastic shield. The respiration monitor 10 also includes a detector housing 24 which is connected to a portion of a strap assembly 26.

The sending end 16 of the sending light conductor 12 is insertable into a portion of the detector housing 24 and the receiving end 20 of the receiving light conductor 18 also is insertable into the detector housing 24. The detector housing 24 is adapted to receive the sending end 16 portion of the sending light conductor 12 and the receiving end 20 portion of the receiving light conductor 18 and to hold and support the portions of the sending and receiving light conductors 12 and 18 insertable therein in a position wherein the sending end 16 of the sending light conductor 12 and the receiving end 20 of the receiving light conductor 18 are spaced apart a distance 28. Further, the detector housing 24 is constructed and adapted and the sending light conductor 12 and the receiving light conductor 18 are supported within the detector housing 24 and connected to the detector housing 24 so that the distance 28 between the receiving end of the receiving light conductor 18 and the sending end 16 of the sending light conductor 12 varies in response to respiration motion of the individual being monitored in a manner for reasons which will be made more apparent below. The receiving end 14 of the sending light conductor 12 and the sending end 22 of the receiving light conductor 18 each are connected to a respiration monitoring control 30. The respiration monitoring control 30 is adapted and constructed to emit light into the receiving end 14 of the sending light conductor 12 and to receive light emitted from the sending end 22 of the receiving light conductor 18 and to provide output indications indicative of respiration motion, in a manner to be described in greater detail below.

In general, the respiration monitor 10 of the present invention particularly is constructed to monitor respiration motion of an individual and to provide output indications indicative of respiration motion. In one preferred embodiment, the respiration monitoring control 30 particularly is adapted to provide an output indication indicative of a cessation or absence of respiration for a predetermined period of time, apnea.

The strap assembly 26 is removeably connectable to a portion of the individual which moves in response to respiration motion of the individual, the strap assembly 26 being strapped about an individual's chest or abdomen for example. The respiration monitoring control 30 includes a portion which emits light into the receiving end 14 of the sending light conductor 12, the sending light conductor 12 conducts such received light therethrough and the light is emitted from the sending end 16 of the sending light conductor 12. The light is emitted across the distance 28 between the sending end 16 of the sending light conductor 12 and the receiving end 20 of the receiving light conductor 18 and the light is received at the receiving end 20 of the receiving light conductor 18. The receiving light conductor 18 conducts the received light generally between the receiving end 20 and the sending 22 thereof and the light is emitted from the sending end 22 of the receiving light conductor 18. The respiration monitoring control 30 receives light emitted from the sending end 22 of the receiving light conductor 18.

During respiration (inhaling and exhaling), the strap assembly 26 is expanded and contracted periodically and the expansion of the strap assembly 26 causes the distance 28 between the sending end 16 of the sending light conductor 12 and the receiving end 20 of the receiving light conductor 18 to be increased, while contraction of the strap assembly 26 causes the distance 28 between the receiving end 20 of the receiving light conductor 18 and the sending end 16 of the sending light conductor 12 to be decreased. An increase in the distance 28 results in a decrease in the intensity of light conducted between the sending end 16 of the sending light conductor 12 to the receiving end 20 of the receiving light conductor 18 and a reduction or decreasing of the distance 28 between the receiving end 20 of the receiving light conductor 18 and the sending end 16 of the sending light conductor 12 results in an increase in the intensity of the light conducted between the sending end 16 of the sending light conductor 12 and the receiving end 20 of the receiving light conductor 18. The respiration monitoring control 30, more particularly, is adapted to receive light from the sending end 22 of the receiving light conductor 18 and to provide output indications indicative of respiration motion in response to determining indications of respiration motion indicated by changes in the intensity of the light received from the sending end 22 of the receiving light conductor 18. In other words, periodic increase and decrease in the distance 28 results in periodic increase and decrease in the intensity of light received by the respiration monitoring control 30 and this periodic increasing and decreasing in the intensity of light received by the respiration monitoring control 30 provides the means for determining respiration motion.

The strap assembly 26, as shown in FIG. 1, comprises a strap 32 having opposite ends 34 and 36. A strip of connecting material 38 is secured to a portion of one side of the strap 32 generally near the end 34 thereof and another strip of connecting material 40 is secured to a portion of one side of the strap 32 generally near the opposite end 36 thereof, the connecting materials 38 and 40 being materials such as Velcro, for example. The connecting materials 38 and 40 are positioned on the strap 32, so when the strap 32 is extended about an individual, the connecting material 38 is disposed generally adjacent the connecting material 40 and the connecting materials 38 and 40 are constructed so that, when the connecting materials 38 and 40 are pressed into contacting engagement, the connecting materials 38 and 40 function to connect the ends 34 and 36 of the strap 32. The end 34 of the strap 32, more particularly, is constructed by connecting an expandable elastic type material extension strip 44 to one end of the strap 32 with the extension strip 44 extending a distance therefrom and forming the end 34 of the strap 32, the connecting material 40 being more particularly connected to the expandable extension strip 44, for reasons which will be made more apparent below.

The strap 32, except for the extension strip 44, is constructed of a flexible, non-elastic or virtually non-expandable type of material, and the strap 32 is constructed of two strips of material with one strip of material being stitched to the other strip of material so that an opening extends between the two strips of material and about the strap 32, the opening being enclosed by the two strip pieces which are stitched together. The sending light conductor 12 extends through the opening in the strap 32 and extends a distance generally about the strap 32, exiting generally from the end 36 of the strap 32 with a portion of the sending light conductor 12 extending a distance from the end 36 of the strap 32 terminating with the sending end 16 of the sending light conductor 12. The opposite end portion of the sending light conductor 12 exits from an opening formed in the strap 32 generally mid-way between the opposite ends 34 and 36 of the strap 32 and the sending light conductor 12 extends a distance from the strap 32 terminating with the receiving end 20 thereof which is connected to the respiration monitoring control 30, the portion of the sending light conductor 12 extending between the strap 32 and the respiration monitoring control 30 being referred to herein as an exposed lead portion 44 of the sending light conductor 12. A portion of the receiving light conductor 18 also extends through the opening formed in the strap 32 and a distance generally about the strap 32 existing from an opening formed in the strap 32 generally near and spaced a distance from the end 34 thereof, the receiving light conductor 18 exiting from the strap 32 and extending a distance therefrom terminating with the receiving end 20 of the receiving light conductor 18. The opposite end portion of the receiving light conductor 18 extends through an opening formed in the strap 32 generally mid-way between the opposite ends 34 and 36, and extends a distance from the strap 32 terminating with the sending end 16 thereof which is connected to the respiration monitoring control 30, the portion of the receiving light conductor 18 extending between the strap 32 and the respiration monitoring control 30 being referred to herein as an exposed lead portion 46.

Figure 2:
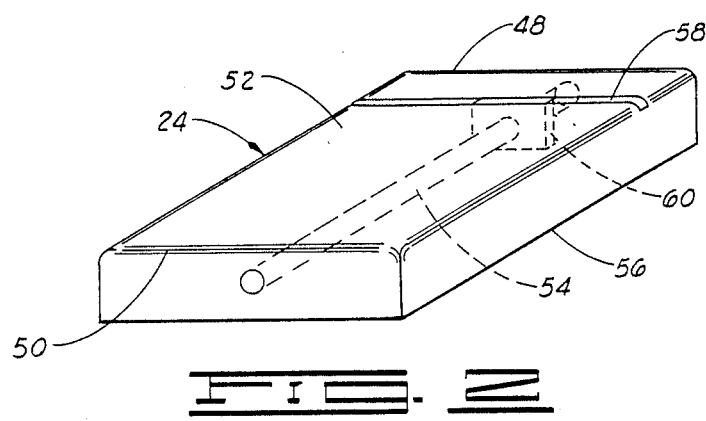
FIG. 2 is a partial perspective view of the detector housing portion of the respiration monitor shown in FIG. 1.

As shown in FIGS. 1 and 2, the detector housing 24 is generally rectangularly shaped and has opposite ends 48 and 50, an upper surface 52 and a lower surface 54. A light opening 56 extends through a portion of the detector housing 24 intersecting the opposite ends 48 and 50 thereof. A filter slot 58 is formed through a portion of the upper surface 52 of the detector housing 24 and the filter slot 58 extends a distance through the detector housing 24 intersecting the light opening 56. The detector housing 24 is constructed of a material opaque to light such as black TFE Teflon, for example.

The filter slot 58 is sized to receive an infrared filter 60. As shown more clearly in FIG. 2, an infrared filter 60 is disposed in the filter slot 58 and positioned so that the filter 60 intersects and extends across the light opening 56. The infrared filter 60 is constructed and adapted to pass substantially only infrared light. After insertion of the filter 60, the filters slot 58 is closed with an opaque cover (not shown). Filters which are constructed and adapted to pass only infrared light in the manner described before with respect to the infrared filter 60 are well known in the art and a detailed description of such a filter is not deemed necessary herein.

The sending end 16 portion of the sending light conductor 12 exits from the strap 32 and is inserted into the portion of the light opening 56 intersecting the end 50 of the detector housing 24, the sending end 16 portion of the sending light conductor 12 extending a distance through the light opening 56 terminating with the sending end 16. The sending end 16 portion of the sending light conductor 12 is movably supported in the detector housing so the sending end 16 portion of the sending light conductor 12 moves generally toward and away from the receiving end 20 of the receiving light conductor 18 during the operation. The receiving end 20 portion of the receiving light conductor 18 exits from the strap 32 and extends into the end of the light opening 56 intersecting the end 58 of the detector housing 24 and the receiving light conductor 18 extends a distance through the light opening 56 terminating with the receiving end 20 thereof, the receiving end 20 portion of the receiving light conductor 18 being secured within the light opening 56 by an epoxy for example to prevent movement of the receiving end 20 portion of the receiving light conductor 18 during the operation. The sending light conductor 12 and the receiving light conductor 18 are each positioned in the detector housing 24 so that the filter 60 is disposed generally between the sending end 16 of the sending light conductor 12 and the receiving end 20 of the receiving light conductor 18.

A protective cover 62 extends about and covers the exposed lead portions 44 and 46 of the receiving light conductor 18 and the sending light conductor 12, respectively. The protective cover 62 is constructed preferably of a flexible material and is intended substantially to prevent the exposed lead portions 44 and 46 from becoming entangled about the individual being monitored during operation of the respiration monitor 10.

In operation, the ends 34 and 36 of the strap 32 are disconnected and the strap 32 is placed about a portion of the individual which moves in response to respiration such as the chest or abdominal area of the individual and the end 34 is brought to a position generally near the end 36 of the strap 32. In this position, the sending end 16 portion of the sending light conductor 12 is inserted into the light opening 56 in the detector housing 24 and the connecting materials 38 and 40 are connected to connect the end 34 to the end 36 of the strap 32, thereby securing the strap 32 about the individual. In this position, the receiving end 20 of the receiving light conductor 18 is disposed the distance 28 from the sending end 16 of the sending light conductor 12, and the infrared filter 60 is disposed between the ends 20 and 16 of the receiving and sending light conductors 18 and 12, respectively.

Light is conducted through the sending light conductor 12, passed from the sending end 16 of the sending light conductor 12 through the infrared filter 60 and received by the receiving end 20 of the receiving light conductor 18. The receiving light conductor 18 conducts such light between the opposite ends thereof and emitts such light from the sending end 22 of the receiving light conductor 18.

As the individual inhales and exhales, the extension strip 44 expands and contracts thereby increasing and decreasing the distance 28 between the receiving end 20 of the receiving light conductor 18 and the sending end 16 of the sending light conductor 12. The increasing of the distance 28 between the receiving end 20 of the receiving light conductor 18 and the sending end 16 of the sending light conductor 12 results in a decrease in the intensity of light received by the receiving end 20 of the receiving light conductor 18, thereby resulting in a decrease in the intensity of light received by the respiration monitoring control 30 from the sending end 22 of the receiving light conductor 18. As the individual exhales, the extension strip 44 contracts thereby decreasing the distance 28 between the receiving end 20 of the receiving light conductor 18 and the sending end 16 of the sending light conductor 12 resulting in an increase in the intensity of light received by the receiving end 20 of the receiving light conductor 18 and an increase of the intensity of the light emitted from the sending 22 of the receiving light conductor 18 and received by the respiration monitoring control 30.

The respiration monitoring control 30 receives light from the sending end 22 of the receiving light conductor 18 and is constructed and adapted to detect respiration motion by detecting periodic increases and decreases in the intensity of light received from the sending end 22 of the receiving light conductor 18. More particularly, the respiration monitoring control 30 is constructed and adapted to provide an alarm signal indicating the cessation or absence of respiration motion (apnea) in response to detecting virtually no change in the intensity of light received from the sending end 22 of the receiving light conductor 18 for a predetermined period of time, such alarm signal being received by an alarm for providing perceivable output indications in response to receiving such an alarm signal in a manner and for reasons to be described in greater detail below.

Shown in FIG. 3 is a modified strap assembly 26a. The modified strap assembly 26a includes a strap 64 having opposite ends 66 and 68. More particularly, the strap 64 is constructed of a flexible, but virtually non-stretchable or non-elastic, material having opposite ends with an extension member 70 being connected to one end thereof, the extension member 70 being constructed of a stretchable, elastic material. The extension member 70 extends a distance and terminates with the end 66 of the strap 64. The detector housing 24 is secured to a portion of the strap 64 and the receiving end 20 of the receiving light conductor 18 and the sending end 16 of the sending light conductor 12 are each inserted and disposed in the detector housing 24 in a manner exactly like that described before with respect to the strap assembly 26 shown in FIG. 1.

The exposed lead portions 44 and 46 of the receiving and sending light conductors 18 and 12, respectively, extend from the detector housing 24. A protective cover 72 extends about the exposed lead portion 44 of the sending light conductor 16 and a protective cover 74 extends about exposed lead portion 46 of the receiving light conductor 18. The protective covers 72 and 74 function to prevent the exposed lead portions 44 and 46 from becoming entangled about the individual during the operation of the respiration monitor in a manner like that described before with respect to the protective cover 62 shown in FIG. 1 and described before.

The strap assembly 26a operates substantially like the strap assembly 26 described before. The strap 64 is positioned about the selected portion of an individual and a connecting material 76 connected to the end 66 portion of the strap 64 is connected to a connecting material 78 connected to the end 68 portion of the strap 64 to connect the opposite ends 66 and 68 of the strap 64 thereby securing the strap 64 about the selected portion of the individual. Then, a connecting material 80 secured to a portion of the sending light conductor 12 generally near the sending end 16 portion of the sending light conductor 12 is secured to a connecting material 82 connected to the end 66 portion of the strap 64 to secure the sending light conductor 12 to the elastic portion of the strap 64 after the sending end 16 of the sending light conductor 12 has been inserted into the light opening 56 formed in the detector housing 24 thereby movably securing the sending light conductor 12 in the proper position disposed in the light opening 56 of the detector housing 24. The opposite ends 14 and 22 of the sending and receiving light conductors 12 and 18, respectively, are connected to the respiration monitoring control 30 in a manner and for reasons exactly like described before in connection with FIG. 1.

The sending light conductor 12 and the receiving light conductor 18 each are identical in construction and each comprises what is commonly referred to in the industry as a fiber optic with a plastic shield. Fiber optics are well known in the art and a detailed description of the construction and operation of such fiber optics is not deemed necessary herein.

It also should be noted that the terms "receiving" and "sending" as well as the terms as "sending end" and "receiving end" as used in connection with the light conductors 12 and 16 are merely for reference and are not intended to describe structural differences in the light conductors 12 and 18.

The respiration monitoring control 30 emits light into the receiving end 14 of the sending light conductor 12 and receives light emitted from the sending end 22 of the receiving light conductor 18. Further, the respiration monitoring control 30 converts the light received from the sending end 22 of the receiving light conductor 18 into an electrical signal in an analog format indicative of the intensity of light received by the receiving end 20 of receiving light conductor 18 or, in other words, indicative of respiration motion, and the respiration monitoring control 30 determines a cessation or absence of respiration motion by determining virtually no change in the intensity of light emitted from the sending end 22 of the receiving light conductor 18 for a predetermined period of time, and the respiration monitoring control 30 provides an alarm signal in response to determining a cessation or absence of respiration motion for the predetermined period of time. One embodiment of a portion of the respiration monitoring control 30 for performing the functions just described is shown in greater detail in FIG. 5.

Figure 4:
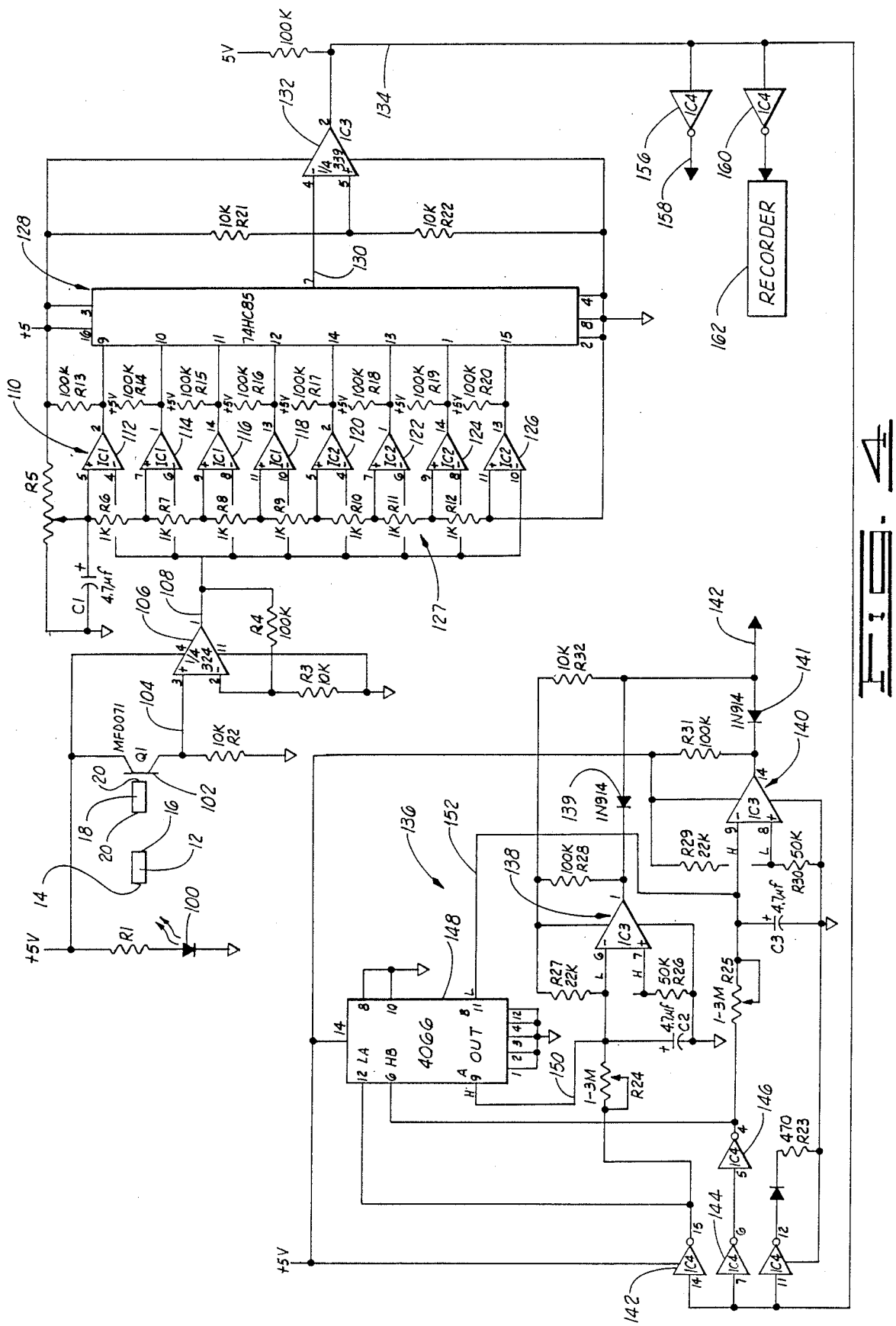
FIG. 4 is a schematic view showing a portion of the respiration monitoring control for providing an alarm signal in response to determining a cessation of respiration.

As shown in FIG. 4, a light emitting diode 100 is positioned near the receiving end 14 of the sending light conductor 12, the light emitting diode 100 being forward biased through a current limiting resistor designated "R1" in FIG. 4. The light emitting diode 100 emits light in the infrared spectrum and this emitted light is received at the receiving end 14 of the sending light conductor 12 and conducted therethrough.

The light conducted through the sending light conductor 12 is emitted from the sending end 16 thereof and modulating in the detector housing 24. The modulated light is received at the receiving end 20 of the receiving light conductor 18 and conducted through the receiving light conductor 18 and emitted from the sending end 22 thereof. The sending end 22 of the receiving light conductor 18 is disposed near the base of a photo-transistor 102 which receives light from the sending end 22 of the receiving light conductor 18 at the base junction, the photo-transistor 102 being adapted to conduct in response to receiving light at the base junction thereof. The photo-transistor 102 and the resistor designated in FIG. 4 by the designation "R2" form a DC amplifier at the junction of the photo-transistors 102 emitter and the resistor "R2", the amplified signal being conducted over a conductor 104. The voltage of the signal on the signal path 104 is indicative of or proportional to the intensity of light received by the photo-transistor 102 from the sending end 20 of the receiving light conductor 18 and, thus, this is an analog signal indicative of respiration motion.

The amplified signal from the photo-transistor 102 is connected to and received by a DC amplifier 106 which receives and amplifies the DC signal outputted by the photo-transistor 102 and outputs the amplified signal over a signal path 108.

The amplified signal on the signal path 108 is an analog signal (a DC signal) which is proportional to the intensity of the light received at the base junction of the photo-transistor 102 or, in other words, the analog signal on the signal path 108 is indicative of and more particularly proportional to the intensity of the light transfered between the sending end 16 of the sending light conductor 12 and the receiving end 20 of the receiving light conductor 18. In one preferred embodiment as shown in FIG. 4, the amplifier 106 is biased to amplify the incoming DC signal by a factor of 10 by way of the resistors designated "R3" and "R4". The amplifier 106 is configured as a non-inverting amplifier and the output of the amplifier is directly coupled to the input of an analog to digital converter 110.

The analog to digital converter 110 is constructed to convert the received analog signal to a digital signal indicative of respiration motion. The analog to digital converter 110 basically consists of two-quad comparators consisting of comparators 112, 114, 116, 118, 120, 122, 124 and 126 connected to a resistor ladder network 127 and a reference adjusting potentiometer designated "R5" in FIG. 4. Each comparator 112 through 126 is referenced to the next comparator 114–126, respectively, in succession by way of the precision resistor ladder network 127. The potentiometer "R5" adjusts the reference voltage supplied to the voltage dividing resistor ladder network 127. The capacitor "C1" functions to stabilize this reference voltage to maintain accuracy in the conversion process.

Each of the comparators 112 through 126 is preset to provide a normally low output signal. When the input to any of the comparators 112–126 exceeds a preset level, the comparators 112–126 provide an output high signal. The signal outputted by the amplifier 106 is inputted to each of the comparators 112–126. If the input signal to the first comparator 112 exceeds a preset minimum, the first comparator 112 outputs a high signal in response thereto. The inputted signal then also is compared by the comparator 114 and if the inputted signal also exceeds the preset minimum of the comparator 114, the comparator 114 also outputs a high signal. The inputted signal sequentially is compared in the same manner by each of the remaining comparators 116, 118, 120, 122, 124 and 126 in response to each inputted signal. In this sequence, if the inputted signal to anyone of the comparators 112–126 does not exceed the preset minimum, the comparator 112–126 outputs a low signal and the remaining comparators 112–126 in the sequence also will output a low signal. The comparators 112–126 thus function to provide a digital output signal indicative of the inputted analog signal outputted by the amplifier 106.

The digital output signal outputted by the analog digital converter 110 is inputted into a magnitude comparator 128. The magnitude comparator 128 compares the magnitude indicated by the digital inputted signals outputted by the analog digital converter 110 and provides an output signal on a signal path 130 which is high or low depending on the magnitude of the inputted signal represented by the digital inputted signal from the analog to digital converter 110. The magnitude comparator 128 is connected to the analog to digital converter 110 so that the output of the magnitude comparator 128 changes from a high to a low or a low to a high state in response to an inputted signal indicating a higher or a lower intensity of the light received at the photo-transistor 102. Thus, assuming the signal initially inputted to the magnitude comparator 128 is such that the magnitude comparator 128 outputs a high signal, the magnitude comparator 128 will output a low signal in response to receiving a next signal from the analog to digital converter 110 indicating a decrease or increase in the intensity of light received from the sending end 22 of the receiving light conductor 18. As the intensity of light received from the sending end 22 of the receiving light conductor 18 increases, the magnitude comparator 128 will alternately output high and low signals. By the same token, as the intensity of light received from the sending end 22 of the receiving light conductor 17 decreases, the magnitude comparator 128 will alternately output high and low signals. Thus, the alternating high and low signals outputted by the magnitude comparator 128 is indicative of respiration motion, while a continuous high or low signal outputted by the magnitude comparator 128 indicates a cessation or absence of respiration motion.

The signal outputted by the magnitude comparator 128 on the signal path 130 is received by a pulse regenerator 132. The pulse regenerator 132 conditions the signal outputted by the magnitude comparator 128 to provide a definite high or low on a pulse regenerator 132 output signal path 134.

Thus, as the individual inhales, the pulse regenerator 132 outputs alternately highs and lows on the signal path 134 and as the individual exhales, the pulse regenerator 132 outputs alternately highs and lows on the signal path 134. The signals outputted by the pulse regenerator 132 on the signal path 134 are inputted into a timer network 136 having a first and a second timer 138 and 140. The first and the second timers 138 and 140, more particularly, are comparators and one input of each of the first and the second timers 138 and 140 is connected to receive the pulses outputted by the pulse regenerator 132 on the signal path 134. More particularly, the first timer 138 receives the pulses outputted by the pulse regenerator 132 by way of an inverter 142 and the second timer 140 receives the pulses outputted by the pulse regenerator 132 by way two inverters 144 and 146 which are connected in series. Thus, when the signal on the signal path 134 is high, the signal inputted to the first timer 138 is low and the signal inputted to the second timer 140 is high and, when the signal on the signal path 134 is low, the signal inputted to the first timer 138 is high and the signal inputted to the second timer 140 is low.

The first and the second timers 138 and 140 each also are connected to an analog switch 148. The pins 8 and 10 (shown in FIG. 4) of the analog switch 148 are grounded. The analog switch 148 is constructed to output a low signal on a signal path 150 or, in other words, to connect the ground to pin 11 in response to a high signal received at pin 12. The analog switch 148 is constructed to output a low signal on a signal path 152, or, in other words, to connect pin 9 to ground in response to a high signal received at pin 6. The low or ground signal on signal path 150 causes a capacitor "C2" to discharge thereby resetting the first timer 138 and a low or ground signal on the signal path 152 causes a capacitor "C3" to discharge thereby resetting the second timer 140.

Assuming the signal on the signal path 134 initially is high, the input to the first timer 138 through the inverter 142 is low and the input to the second timer 140 through the inverters 144 and 146 is high.

The input to pin 12 of the analog switch 148 is thus low, thus pin 11 is in a high impedance state and has no affect on the capacitor C3 of the timer 140. The input to pin 6 of the analog switch 148 is high, thus pin 9 is grounded or low discharging capacitor C2 of the timer 138, this resets timer 138 and also allows the capacitor C3 of the timer 140 to begin charging through resistor R25.

If capacitor C3 of the timer 140 charges to a sufficient level to exceed the voltage reference formed by resistors R29 and R30, then the timer 140 output will change state from a normally high output to a low output.

Next, assume signal on the signal path 134 changes to a low, the input to the first timer 138 through the inverter 142 is high and the input to the second timer 140 through the inverters 144 and 146 is high.

The input to pin 12 of the analog switch 148 is high, thus pin 11 is grounded or low and discharges capacitors C3 of timer 140. This resets timer 140. The input to pin 6 of the analog switch 140 is low, thus pin 9 is in a high impedance state and has no affect on capacitor C2 of the timer 138, this allows capacitor C2 of timer 138 to begin charging through the resistor R24.

If capacitor C2 of the timer 138 charges to a sufficient level to exceed the voltage reference formed by resistors R26 and R27, then the timer 138 output will change state from a normally high to a low output.

As long as the input to the timer network 136 switches between the high and the low states, the timer network 136 will continue to output a high signal on the signal path 142. In the last mentioned example, assume the signal remained in a low state a sufficient period of time for the capacitor C2 to charge, the input to the second timer 140 would be switched to a low state and its capacitor C3 would be discharged since pin 11 of the analog switch 148 would also be low or grounded.

Thus, in this instance, the first timer 138 will output a low, and the second timer 140 will continue to output a high, its normal state. The diodes 139 and 141 along with the resistor R31 are connected to the outputs of both timers 138 and 140. The two diodes and the resistor form an AND gate. As long as both inputs to an AND gate are high, the output will be high, if either input goes low, the output will also be low. Thus, if either timer 138 or 140 outputs a low, the condition of signal path 142 also will be low indicating an absence of respiration motion.

In addition to the signal inputted to the timing network 136, the signal outputted by the pulse regenerator 132 on the signal path 134 is inverted by an inverter 156 an outputted on a signal path 158. Also, the signal outputted by the pulse regenerator 132 on the signal path 134 is passed through an inverter 160 and inputted to a recorder 162. The recorder 162 receives the inverted signal and is constructed and adapted to plot the respiration motion in response to the received signal outputted by the pulse regenerator 132. Recorders which are constructed and adapted to receive signals and plot in an analog format such received signals are commercially available and well known in the art.

Figure 7:
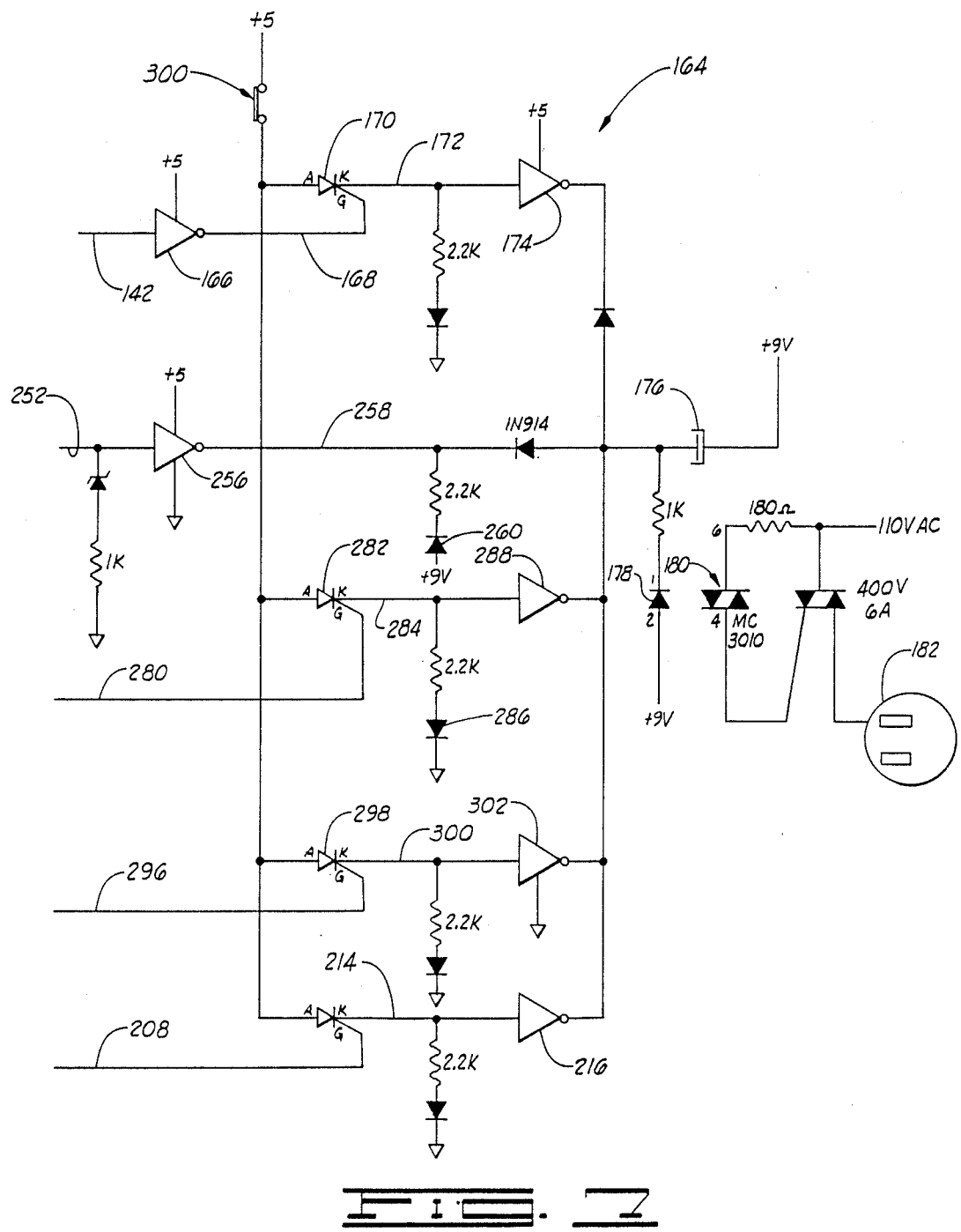
FIG. 7 is a schematic view of the alarm network portion of the respiration monitoring control.

The signal outputted on the signal path 142 is received by an alarm network 164, shown in FIG. 7. As shown in FIG. 7, the output signal on the signal path 142 is inputted to the alarm network 164 through an inverter 166 which outputs a high signal on a signal path 168 in response to receiving a low signal on the signal path 142 indicating an absence of respiration motion. The high signal on the signal path 168 triggers a silicon controlled rectifier 170 which outputs a signal on a signal path 172 causing a light emitting diode 174 to emit light thereby indicating a respiration problem or, in other words, a absence of respiration motion in the monitored individual.

The high signal on the signal path 172 also is inverted by an inverter 174 which outputs a low signal to an alarm buzzer 176 thereby providing an audibly perceivable output indication indicating an absence of respiration motion in the monitored individual.

The low signal outputted by the inverter 174 also causes a light emitting diode 178 to emit light thereby activating an optical coupler 180 and causing a hundred and ten volt output signal to be connected to an external plug 182. The output of the hundred and ten volts at the external plug 182 also indicates an alarm condition or, in other words, an absence of respiration motion in the monitored individual. The plug 186 is provided so that additional alarms may be connected to the alarm network 164. For example, an individual may be deaf and, in this instance, the external plug 182 might be connected to a fluid light which would be lighted in response to the outputting of the hundred and ten volt signal at the external plug 182 for providing a visually perceivable output indication indicating an absence of respiration motion of the monitored individual.

Figure 5:
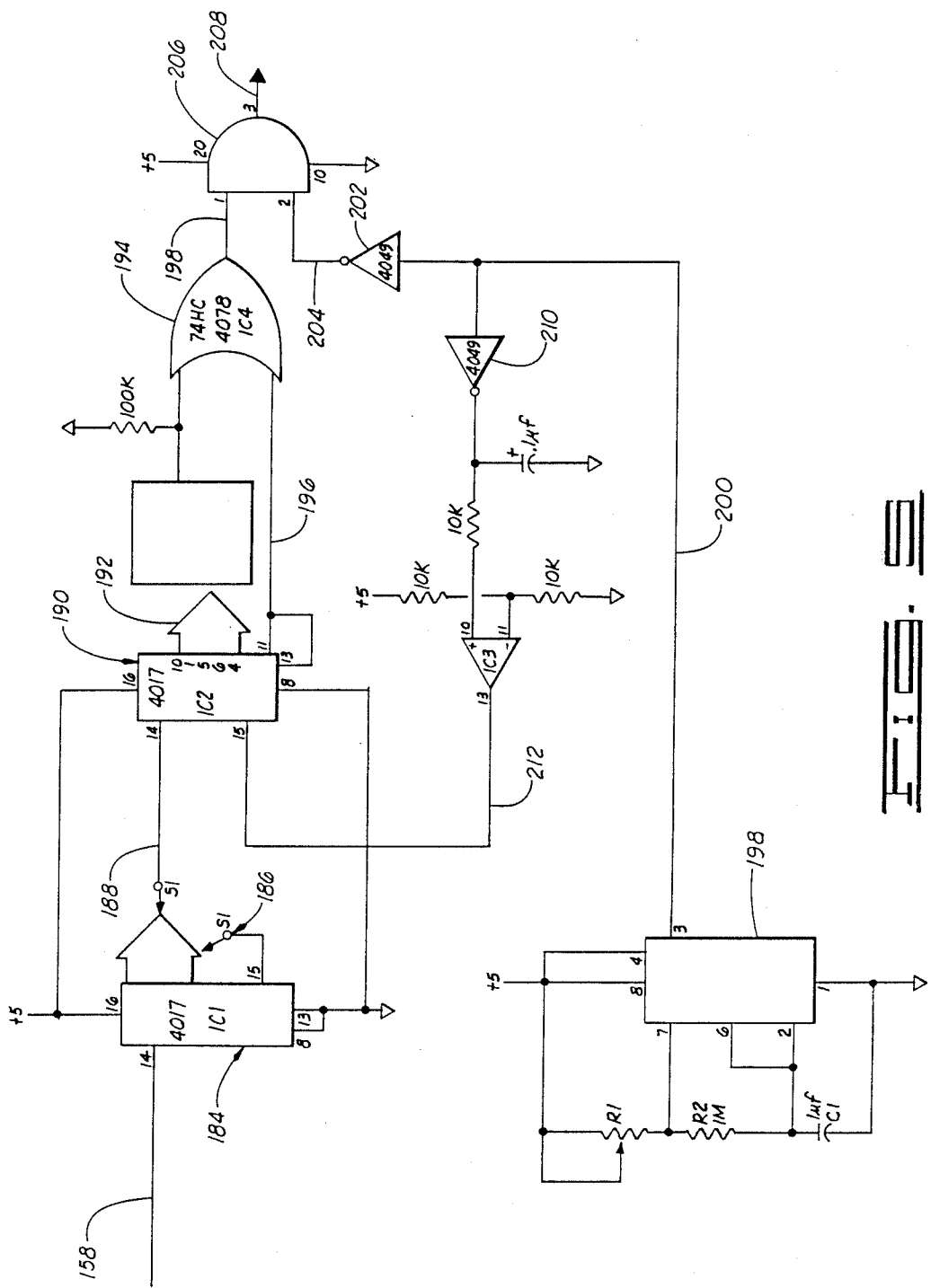
FIG. 5 is a schemmatic view showing a portion of the respiration monitoring control for detecting high respiration rate.
Figure 5:
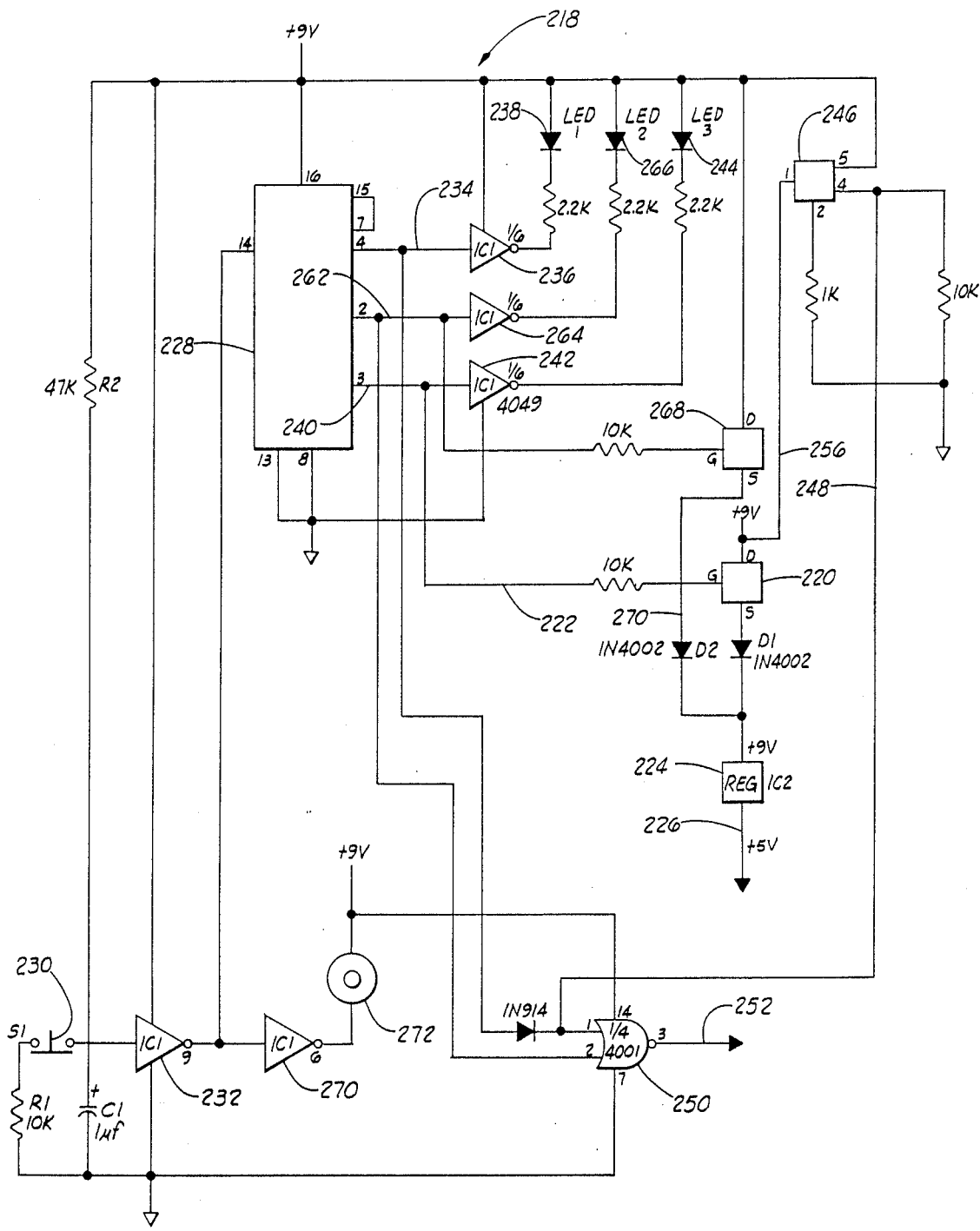

Shown in FIG. 5 is another portion of the respiration monitoring control 30 which is constructed to monitor the respiration rate of the individual and output an alarm signal in response to a detected respiration rate in excess of a predetermined respiration rate. As shown in FIG. 5, the signal outputted by the inverter 156 on the signal path 158 is inputted into a counter 184. The counter 184 receives the inputted pulses on the signal path 158 and divides the inputted pulses by a preselected number 1 through 10 as selected by a selector switch 186. When the counter 184 has received the selected number of input pulses, the counter 186 outputs a high on a signal path 188 which is inputted into a counter 190. The counter 190 outputs a high signal on a signal path 192 in response to a predetermined number of pulses being inputted into the counter 190, the predetermined number being selected by the connection of the signal path 192 to the counter 190 and, in one preferred embodiment, the last five outputs of the counter 190 are connected to the signal path 192 so that, when the counter 192 counts five or more inputted pulses, the counter 192 outputs a high pulse on the signal path 192 which is received by an OR gate 194. A signal path 196 also is connected to the counter 190 and the counter 190 outputs a high signal on the signal path 196 in response to the counter 190 receiving and counting ten input pulses before being reset. Thus, if the counter 190 receives five or more pulses, the counter will output a high signal on the signal path 192 which is inputted to the OR gate 194 and the OR gate 194 outputs a high signal on a signal path 198 in response to receiving an inputted high signal on the signal path 192.

A pulse generator 198 is adapted to provide an output low signal on a signal path 200 periodically, the outputted low signal having a predetermined duration and being provided periodically every predetermined period of time. For example, in one embodiment, the timer 198 is constructed and adapted to provide an output low signal having a duration of fifty milliseconds every ten seconds. The outputted low signal provided by the pulse generator 198 is inverted by an inverter 202 which provides an outputted high signal on the signal path 204 which is received by an AND gate 206. The AND gate 206 also receives the signal on the signal path 198 and the AND gate 206 provides an output high signal on a signal path 208 in response to receiving a high signal on the signal path 198 and a high signal on the signal path 204. The pulse generator 198 output on the signal path 200 also is inverted by an inverter 210 which provides the inverted signal on a signal path 212, the signal path 212 being connected to the counter 190 for resetting the counter 190 in response to receiving a high signal on the signal path 212. Thus, in the one embodiment mentioned before, the pulse generator 198 outputs a low signal every ten seconds which is inverted by the inverter 210 to provide a high signal for resetting the counter 190 every ten seconds. The capacitor and resistor at the inverter 210 output provide a delay circuit for resetting the counter 190.

Assuming the counter 190 has received a predetermined minimum inputted pulses before being reset by the pulse generator 198, thereby indicating a predetermined high respiration rate in the monitored individual, the counter 190 outputs a high signal on the signal path 192 which is inputted through the OR gate 194 to the AND gate 206. When the AND gate 206 also receives a high signal on the signal path 204, the AND gate 206 outputs a high signal, an alarm signal, on the signal path 208 thereby indicating a high respiration rate in the individual being monitored. The AND gate 206 will receive a high signal every ten seconds in the embodiment just described and thus the AND gate 206 will output the high signal on the signal path 204 in response to the low signal being outputted by the pulse generator 198, the pulse generator 198 output signal in the low state on the signal path 200 also acting to reset the counter 190.

The outputted high signal on the signal path 208 indicating a high respiration rate in the individual being monitored is inputted to the alarm network, shown in FIG. 7. The high signal on the signal path 208 triggers a silicon control rectifier 212 which provides a high signal on a signal path 214 which is inverted by an inverter 216. The inverter 216 outputs a low signal thereby activating the alarm 176 to provide the audibly perceivable output indication and activating the light emitting diode 178 for causing the hundred and ten volt signal to be connected to the external plug 182 for activating an external alarm device (not shown) in the manner and for reasons mentioned before with respect to the inputted high signal on the signal path 142.

Shown in FIG. 6 is a power supply select and power failure circuit 218. An unregulated nine volt power supply is connected to a power transistor 220, and when the power transistor 220 is "on" in response to receiving a high signal on a signal path 222, the power transistor 220 passes the nine volt unregulated power supply through to a voltage regulator 224. The regulated power supply outputted on a signal path 226 from the voltage regulator 224 provides operating power supply to the various circuits of the respiration monitoring control 30.

The power supply select and power failure circuit 218 includes a ring counter 228 which is constructed and adapted to provide only one output high signal in any given state. The ring counter 228 is connected to a function switch 230 by way of an inverter 232. When the function switch 232 is momentarily depressed, a high signal is inputted into the ring counter 228 for changing the outputted signal of the ring signal 228. For example, assume that the ring counter 228 is initially conditioned to output a high signal on a signal path 234 indicating that the power is "off" or, in other words, power is not being supplied to the remaining circuits of the motion monitoring control. In this state of the ring counter 228, the outputted high signal on the signal path 234 is inverted by an inverter 236 and the outputted low signal from the inverter 236 causes the light emitting diode 238 to be illuminated thereby providing a visually perceivable output indication indicating that the respiration monitoring control 30 is in the "off" condition.

Assuming it is desirable to turn the motion monitoring control 30 "on", the individual depresses the function switch 230 twice to provide an output high signal on a signal path 240 which is inverted by an inverter 242. The inverter 242 output signal in the low state illuminates a light emitting diode 244 thereby providing a visually perceivable output indication indicating that the respiration monitoring control 30 is "on" and operating with line power supply. The outputted high signal on the signal path 240 also is connected to the switching transistor 220 by way of the signal path 222 for biasing the switching transistor 220 "on" thereby providing power to the components of the respiration monitoring control 30 through the regulator 224.

As long as the signal on the signal path 248 remains in the high state, the NOR gate outputs a signal on a signal path 252 in the low state. Power is provided to the optical coupler 246 by way of a signal path 256 and, as long as power is provided to the optical coupler 246 by way of the signal path 256, the optical coupler 256 is powered "on" and an output high signal is provided on the signal path 248. If for some reason there is a power failure, then power is not provided to the optical coupler 246 and an output low signal is provided on the signal path 248 and the NOR gate 258 outputs a high signal, an alarm signal, indicating a power failure on the signal path 252.

The signal path 252 is connected to the alarm network 164, as shown in FIG. 7. The outputted high signal on the signal path 252 is inverted by an inverter 256 which outputs a low signal on a signal path 258. The outputted low signal on the signal path 258 illuminates a light emitting diode 260 thereby providing a visually perceivable output indication indicating a power failure in the power supply for the respiration monitoring control 30. In addition, the outputted low signal on the signal path 258 activates the alarm 176 to provide an audibly perceivable output indication indicating a power failure and the outputted low signal on the signal path 258 also causes the one hundred and ten volts supply to be connected to the external plug 182 in a manner for reasons described before.

If there is a power failure, the operator can depress the function switch 230 thereby causing the ring counter 238 to output a high signal on a signal path 262 which is passed through an inverter 264. The low signal outputted by the inverter 264 causes a light emitting diode 266 to be illuminated thereby providing a visually perceivable output indication indicating that the respiration monitoring control 30 is operating on a battery power supply. The high signal on the signal path 264 is connected to a power switching transistor 268 thereby conditioning the switching transistor 268 in the "on" condition. In the "on" condition of the switching transistor 268, the switching transistor 268 functions to pass the nine volt battery supply through to an output signal path 270 thereby connecting the battery supply to the voltage regulator 244, the voltage regulator 244 functioning to regulate the nine volt battery power supply and outputted regulated power supply on the signal path 226 provides power for operating the components of the respiration monitoring control 30.

The ring counter 228 output signals on the signal path 234 and 262 each are connected to the NOR gate 250. Thus, when the power supply select and power failure circuit 218 is functioning to operate the components of the respiration monitoring control 30 on line power supply, the input to the NOR gate 250 on the signal path 262 is in the high state and the other input to the NOR gate 250 is in the high state, the NOR gate 250 providing an output low signal in this condition. The NOR gate 250 will continue to provide an output low signal unless there is a loss of power resulting in a low signal being inputted to the NOR gate on the signal path 248 which results in the NOR gate 250 outputting the high signal indicating a power failure and activating the alarm network 164 in the manner described before.

When the function switch 230 has conditioned the ring counter 228 to output a high signal on the signal path 262 for connecting the battery power supply to the components of the respiration monitoring control 30, the NOR gate 250 receives an input high signal on the signal path 262 and an input low signal on the signal path 248 results in the NOR gate 250 outputting a low signal on the signal path 252. The battery also is connected to the ring counter 228 and, thus, if the battery also were to fail, the signal on the signal path 262 then would go to a low state and the NOR gate 250 would output a signal in the high state on the signal path 252 for providing the visually perceivable and audible perceivable alarm output indications by the alarm network 164 in the manner described before indicating a power failure.

When the function switch 230 is momentarily depressed, the low signal provided by the inverter 232 is inverted by an inverter 270 to provide a high signal to a beeper 272 which provides an audibly perceivable output indication indicating that the function switch 230 has been depressed. The audible output indication provided by the beeper 272 will continue as long as the operator holds the function switch 230 in the depressed condition. The beeper 272 merely provides an audible output indication for the operator indicating to the operator that the function switch 230 is being operated or depressed.

The nine volt battery supply also is connected to a low battery network 274 shown in FIG. 8 by way of a voltage divider 276. The voltage divider 276 output is inputted to an inverter 278. As long as the battery has sufficient power, the battery operates to input through the voltage divider network 276 a high signal and the inverter 278 functions to provide an output low signal on a signal path 280. When the battery power supply reaches a predetermined low level, the battery voltage applied across the voltage divider 276 operates to output a low signal which is inputted to the inverter 278, the inverter 278 outputting a high signal, an alarm signal, on the signal path 280 in response to and indicating a low condition of the battery power supply. The signal path 280 is connected to the alarm network 164 shown in FIG. 7. The high signal on the signal path 280 indicating a low battery condition activates a silicon control rectifier 282 thereby resulting in an outputted high signal on a signal path 284. The outputted high signal on the signal path 284 causes a light emitting diode 286 to be illuminated thereby providing a visually perceivable output indication indicating a low battery condition. In addition, the outputted high signal on the signal path 284 is inverted by an inverter 288 and the inverter 288 functions to output a low signal which activates the alarm 176 to provide the audibly perceivable output indication indicating a low battery condition and to connect the one hundred and ten volt supply to the external plug 182 in the manner and for reasons described before.

The respiration monitoring control 30 also includes a tampering control 290 shown in FIG. 9. The tampering control 290 includes a plurality of contacts, only one set of the contacts being shown in FIG. 9 and designated therein by the generally reference numeral 292. Each pair of contacts is connected to the tampering control 290 exactly as shown in FIG. 9 with respect to the one set of contacts 292. Each pair of contacts is positioned near one of the external switches or controls operating the respiration monitoring control 30 and each pair of contacts is normally open.

If an individual attempts to change the setting of any of the switches or controls of the respiration monitoring control 30, the individual will cause the contacts to be closed thereby causing a flip-flop 294 to output a high signal on a signal path 296 which is inputted to the alarm network 164 shown in FIG. 7. The outputted high signal on the signal path 296 activates a silicon control rectifier 298 for providing a high signal on a signal path 300. The outputted high signal on the signal path 300 is inverted by an inverter 302 and the inverter 302 outputs a low signal which activates the alarm 176 for providing an audibly perceivable output indication indicating a tampering condition. In addition, the low signal outputted by the inverter 302 also connects the one hundred and ten volt power supply to the external plug 182 in the manner and for reasons mentioned before.

The alarm network 164 includes a normally closed momentary reset switch 300, as shown in FIG. 7. After the alarm network 164 has been activiated by any one of the alarm signals, the various alarms and indicators only can be deactivated by depressing the reset switch 300 and the reset switch 300 must be depressed to deactivate the various alarms and indicators which automatically resets the alarm network 164 for receiving another alarm signal.

The various individual components of the respiration monitoring control 30 are commercially available from various sources. Some of the components are listed below along with a manufacturer name and model number indicating the source of these particular components.

| NUMBER | DESCRIPTION | MANU-FACTURER | MODEL NO. |
|---|---|---|---|
| 100 | Light Emitting Diode | Motorola | MFE071 |
| 102 | Photo-transistor | Motorola | MFD071 |
| 106 | Amplifier | National Semiconductor | LM324 |
| 112-126 | Comparators | National Semiconductor | LM339 |
| 128 | Magnitude Comparator | Texas Instruments | 74HC85 |
| 132 | Pulse Regenarator | National Semiconductor | LM339 |
| 138-140 | Timers (IC3) | National Semiconductor | LM339 |
| 176 | Alarm | | |
| 184 | Counter | Texas Instruments | 4017 |
| 190 | Counter | Texas Instruments | 4017 |
| 198 | Pulse Generator | Texas Instruments | 555 |
| 228 | Ring Counter | Texas Instruments | 4017 |
| 220 | Power Transistor | National Semiconductor | BS170 |
| 246 | Optical Coupler | Motorola | MC3010 |
| 268 | Switching | National | BS170 |

-continued

| NUMBER | DESCRIPTION | MANU-FACTURER | MODEL NO. |
|---|---|---|---|
| 272 | Transistor Beeper | Semiconductor Sonalert | |

It is significant to note that the sending light conductor 12 and the receiving light conductor 18 preferably are fiber optics with a plastic shield. The inherent noise immunity of fiber optics in long transmission lines provides one distinct advantage over metallic transmission facilities. Due to this property of fiber optics, the electronics used may be simpler in construction due to the fact that no filtering of the incoming signal generally is required. Due to the fact that fiber optics are not conductors of emf. This features is of significance in medical applications such as with the respiration monitor 10 of the present invention because the patient is completely isolated from any danger of shock from common mode sources, all of the electronic controls and electrical components being located in the respiration monitoring control 30 which is remotely located with respect to the apparatus in contact with the individual being monitored. The electronics connected to the fiber optics also are protected from sources of destructive electrical current that the patient may be subject to such as defibrillation devices.

The respiration monitor 10 of the present invention provides a virtually completely safe monitor, in the sense of protection from any possibility of electrical shock, and provides a sensitive respiration monitor for responding to respiration and distinguishing normal rates of respiration from struggling due to the patient's inability to breath.

The respiration monitor 10 of the present invention also provides a self-adjusting electronic circuitry in the respiration monitoring control 30 which will allow simple connection of the device without the need for constant re-adjustment by the nurse or patient.

The respiration monitor 10 of the present invention also eliminates the need for electrodes, commonly used in conjunction with apnea monitors since these cause irritation of the skin of the patient using them.

The respiration monitor 10 of the present invention also provides distinct and separate alarms for not only apnea episodes, and struggling for breath, but also for power failure, low battery indications, sibling tampering, and external alarms which are connected to each of the last mentioned alarms for remote signaling of those in attendance upon the patient.

The respiration monitor 10 of the present invention also provides an indication of the period of time since the last apnea episode has begun to occur.

The respiration monitor 10 also provides the recorder 162 for recording respiration motion of the patient thereby providing a historical record.

The alarm network 164 is constructed so that must be manually reset by the operator to substantially prevent the happening of an apnea episode undetected.

The respiration monitor 10 provides a basic device that will monitor apnea, struggling, power failure, low battery, tampering and external optional alarm. The respiration monitor 10 also provides versatility due to being able to use the device with either alternating current power or with battery power. The circuit is being designed to draw less than 12 milliamps of power making it ideal for battery operation. However, the distinct advantage of using fiber optics is that, when the device is used with a source of alternating current power, only one small battery is necessary in order to provide power failure indications. All other functions are performed by line current unless switched to battery power. This is a distinct advantage over present apnea monitors that require expensive battery packs that must be recharged, which require another expensive back-up battery pack or dangerous down time when other monitors could not be used due to reliance upon batteries.

It should be noted that in some applications it may be desirable to utilize a single fiber optic for the sending and receiving light conductors. In this instance, the light would be reflected from a reflecting medium and returned to the same fiber optic.

Changes may be made in the construction and operation of the various elements and components described herein and changes may be made in the steps or sequences of steps of the methods described herein without departing from the spirit and scope of the invention as defined in the following claims.

What is claimed is:

1. A respiration monitor for monitoring respiration motion of a individual, comprising:
    a sending light conductor having a receiving end and a sending end, the sending light conductor being suitable for conducting light between the receiving and sending ends thereof;
    a receiving light conductor having a receiving end and a sending end, the receiving light conductor being suitable for conducting light between the receiving and sending ends thereof;
    light conductor support means, the sending end portion of the sending light conductor being affixed to the light conductor support means and the receiving end of the receiving light conductor being disposed on the light conductor support means with the sending light conductor and the receiving light conductor being positioned so that the sending end of the sending light conductor is spaced a distance from and in alignment with the receiving end of the receiving light conductor said support means being constructed to maintain substantial linear alignment at all times whereby the light passing therebetween will at all times define a substantially straight line,
    means for positioning the light conductor support means near a portion of the individual which moves in response to respiration motion of the individual and for varying the distance between the sending end of the sending light conductor and the receiving end of the receiving light conductor in response to respiration motion;
    a light source for emitting light, the light source and being positioned near the receiving end of the sending light conductor and the sending light conductor receiving light from the light source and conducting such received light therethrough toward the sending end of the sending light conductor and the light being emitted from the sending end of the sending light conductor, the receiving end of the receiving light conductor receiving light from the sending end of the sending light conductor and conducting such received light therethrough toward the sending end of the receiving light conductor and the light being emitted from the sending end of the receiving light conductor, the intensity of the light receiving by the receiving end and emitted from the sending end of the receiving light conductor being indicative of the distance between the sending end of the sending light conductor and the receiving end of the receiving light conductor; and
    means for receiving light from the sending end of the receiving light conductor and determining indications or respiration motion in response to changes in the intensity of the received light and providing an output indication indicative of respiration motion.

2. The respiration monitor of claim 1 wherein the means providing the output indication indicative of respiration motion is defined further an determining an absence of respiration motion in response to determining substantially no change in the intensity of received light for a predetermined period of time.

3. The respiration monitor of claim 2 wherein the means for receiving light from the sending end of the receiving light conductor is defined further to include:
    means for receiving light from the sending end of the receiving light conductor and providing an output electrical analog signal indicative of the intensity of light received from the receiving light conductor; and
    means for receiving the electrical analog signal indicative of the intensity of the light received from the receiving light conductor and for providing an output alarm signal in response to substantially no change in the received electrical analog signal for a predetermined period of time.

4. The respiration monitor of claim 3 defined further to include:
    alarm means receiving the alarm signal and providing a perceivable output indication in response to receiving the alarm signal.

5. The respiration monitor of claim 1 wherein the means for receiving light from the sending end of the receiving light conductor and determining indications of respiration motion is defined further to include:
    means for converting the light received from the sending end of the receiving light conductor to a digital signal indicative of the intensity of the light received from the sending end of the receiving light conductor; and
    means for receiving the digital signal indicative of changes in the intensity of the light received from the sending end of the receiving light conductor and providing an output alarm signal in response to determining no change in the state of the received digital signal for a predetermined period of time thereby indicating an absence of respiration motion for the predetermined period of time.

6. The respiration monitor of claim 5 wherein the means for receiving light from the sending end of the receiving light conductor and determining indication of respiration motion is defined further to include:
    means for receiving the alarm signal indicative of an absence of respiration motion for the predetermined period of time and providing an audibly perceivable output indication indicating an absence of respiration motion for the predetermined period of time; and
    means for receiving the alarm signal indicative of absence of respiration motion for the predetermined period of time and providing a visually perceivable output indication indicative of an absence of respiration motion for the predetermined period of time.

7. The respiration monitor of claim 5 defined further to include:
   means for receiving the digital signal indicative of changes in the intensity of light received from the sending end of the receiving light conductor and determining the respiration rate of the individual being monitored.

8. The respiration monitor of claim 1 wherein the means for receiving light from the sending end of the receiving light conductor and determining indications of respiration motion is defined further to include:
   means for providing an operating power;
   means for determining the operating power is being provided and for determining the absence of providing the operating power supply, said means providing an output alarm signal in response to determining an absence of providing the operating power.

9. The respiration monitor of claim 8 wherein the means for providing operating power is defined further to include a line operating power supply and a battery operating power supply, and wherein the means for receiving light from the sending end of the receiving light conductor and determining indications of respiration motion is defined further to include:
   means for selectively switching to one of the battery operating power supply and to the line operating power supply for providing the operating power.

10. The respiration monitor of claim 1 wherein the sending light conductor and the receiving light conductor each are defined further as being constructed of fiber optics.

11. A respiration monitor for monitoring respiration motion of an individual, comprising:
   a sending light conductor having a receiving end and a sending end, the sending light conductor being suitable for conducting light between the receiving and sending ends thereof;
   a receiving light conductor having a receiving end and a sending end, the receiving light conductor being suitable for conducting light between the receiving and sending ends thereof;
   means for positioning the sending end of the sending light conductor generally near and spaced a distance from the receiving end of the receiving light conductor, and for positioning the sending end portion of the sending light conductor and the receiving end portion of the receiving light conductor near a portion of the individual which moves in response to respiration motion of the individual, and for holding the sending end of the sending light conductor and the receiving end of the receiving light conductor so the distance between the sending end of the sending light conductor and the receiving end of the receiving end of the receiving light conductor varies in response to respiration motion of the individual;
   a light source for emitting light, the light source and being positioned near the receiving end of the sending light conductor and the sending light conductor receiving light from the light source and conducting such received light therethrough toward the sending end of the sending light conductor and the light being emitted from the sending end of the sending light conductor, the receiving end of the receiving light conductor receiving light form the sending end of the sending light conductor and conducting such received light therethrough toward the sending end of the receiving light conductor and the light being emitted from the sending end of the receiving light conductor, the intensity of the light received by the receiving end and emitted from the sending end of the receiving light conductor being indicative of the distance between the sending end of the sending light conductor and the receiving end of the receiving end of the receiving light conductor; and
   means for receiving light from the sending end of the receiving light conductor and determining indications of respiration motion in response to changes in the intensity of the received light and providing an output indication indicative of respiration motion, comprising:
   means for converting the light received from the sending end of the receiving light conductor to a digital signal indicative of the intensity of the light received from the sending end of the receiving light conductor; and
   means for receiving the digital signal indicative of changes in the intensity of the light received from the sending end of the receiving light conductor and providing an output alarm signal in response to determining no change in the state of the received digital signal for a predetermined period of time thereby indicating an absence of respiration motion for the predetermined period of time;
   means for receiving the digital signal indicative of changes int eh intensity of light received from the sending end of the receiving light conductor and determining the respiration rate of the individual being monitored; and
   means for providing an output alarm signal in response to determining the respiration rate of the individual being monitored at a level above a predetermined respiration rate.

12. The respiration monitor of claim 11 wherein the means for receiving light from the sending end of the receiving light conductor and determining indications of respiration motion is defined further to include:
   means for receiving the alarm signal indicative of a determined high respiration rate and providing a visually perceivable output indication indicating a determined high respiration rate of the individual being monitored; and
   means for receiving the alarm signal indicative of a determined high respiration rate of the individual being monitored and providing an audibly perceivable output indication indicating a determined high respiration rate of the individual being monitored.

13. The respiration monitor of claim 12 wherein the means for receiving light from the sending end of the receiving light conductor and determining indications of respiration motion is defined further to include:
   means for receiving the alarm signal indicating the absence of providing a regulated power supply and for providing a visually perceivable output indication indicating the absence of providing a operating power; and
   means for receiving the alarm signal indicating the absence of providing the operation power and providing an audibly perceivable output indication indicating the absence of providing the operating power.

14. A method for monitoring respiration motion of an individual utilizing light conductor support means, a sending light conductor having the receiving end and a sending end and a receiving light conductor having a receiving end and a sending end, the receiving light conductor and the sending light conductor each being suitable for conducting light between the respective receiving and sending ends thereof, comprising the steps of:

> positioning the sending end of the sending light conductor and the receiving end of the receiving light conductor on the light conductor support means with the sending end of the sending light conductor being spaced a distance form and in alignment with the receiving end of the receiving light conductor, said support means being constructed to maintain substantially linear alignment at all times whereby the light passing therebetween will at all times define a substantially straight line;
>
> positioning the sending end of the sending light conductor and the receiving end of the receiving light conductor near a portion of the individual which moves in response to respiration motion whereby the distance between the sending end of the sending light conductor and the receiving end of the receiving light conductor varies in response to respiration motion of the individual;
>
> conducting light through the sending light conductor, the light being emitted from the sending end of the sending light conductor and being received by the receiving end of the receiving light conductor and the intensity of the light received by the receiving light conductor being indicative of the distance between the sending light conductor and the receiving end of the receiving light conductor; and
>
> receiving light from the sending end of the receiving light conductor and determining indications of respiration motion in response to changes in the intensity of the light received from the sending end of the receiving light conductor.

15. The method for claim 14 defined further to include the steps of:

> converting the light received from the sending end of the receiving light conductor to digital signals indicative of changes in the intensity of light received from the sending end of the receiving light conductor thereby being indicative of respiration motion and providing an output indication indicative of respiration motion.

16. The method of claim 14 defined further to include the steps of:

> converting the light received from the sending end of the receiving light conductor to digital signals indicative of changes in the intensity of light received from the sending end of the receiving light conductor thereby being indicative of respiration motion and determining an absence of respiration motion in response to determining an absence of change of state of the digital signal for a predetermined period of time and providing an output alarm signal in response to determining an absence of respiration motion for the predetermined period of time.

17. The method of claim 16 defined further to include the steps:

> receiving the alarm signal indicative of an absence of respiration motion and providing a visually perceivable output indication indicating an absence of respiration motion for the predetermined period of time; and
>
> receiving the alarm signal indicative of an absence of respiration motion and providing an audibly perceivable output indication indicating an absence of respiration motion for the predetermined period of time.

18. The method of claim 15 defined further to include the steps:

> receiving the digital signal indicative respiration motion and determining the respiration rate of the individual being monitored.

19. The method of claim 18 defined further to include the steps:

> providing an output alarm signal in response to determining the respiration rate of an individual above a predetermined high respiration rate; and
>
> receiving the alarm signal indicative of a high respiration rate and providing a visually perceivable output indication indicating a determined high respiration rate; and
>
> receiving the alarm signal indicating a high respiration rate and providing an audibly perceivable output indication indicating a determined high respiration rate.

20. The method of claim 14 wherein the sending and receiving light conductors each are defined further as being fiber optics.

21. A method for determining motion utilizing light conductor support means, a sending light conductor having a receiving end and a sending end and a receiving light conductor having a receiving end and a sending end, the receiving light conductor and the sending light conductor each being suitable for conducting light between the respective receiving and sending ends thereof, comprising the steps of:

> positioning the sending end of the sending light conductor and the receiving end of the receiving light conductor on the light conductor support means with the sending end of the sending light conductor being spaced a distance from and in alignment with the receiving end of the receiving light conductor said support means being constructed to maintain substantial linear alignment at all times whereby the light passing therebetween will at all times define a substantially straight line;
>
> positioning the sending end of the sending light conductor and the receiving end of the receiving light conductor with respect to the motion being monitored whereby the distance between the sending end of the sending light conductor and the receiving end of the receiving light conductor varies in response to the motion;
>
> conducting light through the sending light conductor, the light being emitted from the sending end of the sending light conductor and being received by the receiving end of the receiving light conductor and the intensity of the light received by the receiving light conductor being indicative of the distance between the sending end of the sending light conductor and the receiving end of the receiving light conductor; and
>
> receiving light from the sending end of the receiving light conductor and determining indications of motion in response to changes in the intensity of light received from the sending end of the receiving light conductor.

22. The method of claim 21 wherein the sending light conductor and the receiving light conductor each are defined further as being fiber optics.

23. A respiration monitor for monitoring respiration motion of an individual, comprising:
- a sending light conductor having a receiving end and a sending end, the sending light conductor being suitable for conducting light between the receiving and sending ends thereof;
- a receiving light conductor having a receiving end and a sending end the receiving light conductor being suitable for conducting light between the receiving and sending ends thereof;
- means for positioning the sending end of the sending light conductor generally near and spaced a distance from the receiving end of the receiving light conductor, and for positioning the sending end portion of the sending light conductor and the receiving end portion of the receiving light conductor near a portion of the individual which moves in response to respiration motion of the individual, and for holding the sending end of the sending light conductor and the receiving end of the receiving light conductor so the distance between the sending end of the sending light conductor and the receiving end of the receiving end of the receiving light conductor varies in response to respiration motion of the individual, said means comprising:
  - a detector housing having a light opening extending a distance therethrough, the sending end portion of the sending light conductor being insertable into the light opening and the receiving end of the receiving light conductor being insertable into the light opening with the sending light conductor and the receiving light conductor being positioned in the detector housing so the sending end of the receiving light conductor is spaced a distance from the receiving end of the receiving light conductor; and
  - a strap assembly having the detector housing connected to a portion thereof, the strap assembly being removably attachable to the individual for removable positioning the detector housing generally near the portion of the individual which moves in response to respiration of the individual;
- a light source for emitting light, the light source being positioned near the receiving end of the sending light conductor and the sending light conductor receiving light from the light source and conducting such received light therethrough toward the sending end of the sending light conductor and the light being emitted from the sending end of the sending light conductor, the receiving ed of the receiving light conductor receiving light from the sending end of the sending light conductor and conducting such received light therethrough toward the sending end of the receiving light conductor and the light being emitted from the sending end of the receiving light conductor, the intensity of the light received by the receiving end and emitted from the sending end of the receiving light conductor being indicative of the distance between the sending end of the sending light conductor and the receiving end of the receiving end of the receiving light conductor; and
- means for receiving light from the sending end of the receiving light conductor and determining indications of respiration motion in response to changes in the intensity of the received light and providing an output indication indicative of respiration motion.

24. The respiration monitor of claim 23 wherein the means providing the output indication indicative of respiration motion is defined further as determining an absence of respiration motion in response to determining substantially no change in the intensity of received light for a predetermined period of time.

25. The respiration monitor of claim 23 wherein the light source is defined further as being adapted to emit infrared light, and wherein the detector housing is defined further to include a filter slot formed through a portion thereof, a portion of the filter slot intersecting the light opening in the detector housing, and wherein the means for positioning the sending and receiving light conductors generally near a portion of the individual is defined further to include:
- an infrared filter disposed in the filter slot in the detector housing, the filter slot being positioned in the detector housing so that infrared filter is positioned generally between the sending end of the sending light conductor and the receiving end of the receiving light conductor and the infrared filter being adapted to pass substantially only infrared light.

26. The respiration monitor of claim 25 wherein the receiving end portion of the receiving light conductor is defined further as being connected to the detector housing so that the receiving end portion of the receiving light conductor is not movable with respect to the detector housing, and wherein the sending end portion of the sending light conductor is defined further as being movably disposed in the light opening in the detector housing, the sending end portion of the sending light conductor being movable in the detector housing in response to respiration motion of the individual, thereby increasing and decreasing the distance between the sending end of the sending light conductor and the receiving end of the receiving light conductor in response to respiration motion.

27. The respiration monitoring of claim 23 wherein the receiving end portion of the receiving light conductor is defined further as being connected to the detector housing so that the receiving end portion of the receiving light conductor is not movable with respect to the detector housing, and wherein the sending end portion of the sending light conductor is defined further as being movably disposed in the light opening in the detector housing, the sending end portion of the sending light conductor being movable in the detector housing in response to respiration motion of the individual.

28. The respiration monitor of claim 23 wherein the strap assembly is defined further to include:
- a strap having opposite ends, the detector housing being connected to the strap, generally near one end thereof, one end portion of the strap being removably attachable to a portion of the strap, generally near the opposite end thereof.

29. The respiration monitor of claim 28 wherein a portion of the receiving light conductor extends through a portion of the strap with a portion of the receiving light conductor exiting from the strap and extending a distance terminating with the sending end thereof, an exposed lead portion of the receiving light conductor, and wherein a portion of the sending light conductor extends through a portion of the strap with a portion of the sending light conductor generally near the sending end exiting form the strap and a portion of the sending light conductor exiting from the strap and extending a distance terminating with the receiving end thereof, an exposed lead portion of the sending light conductor.

30. The respiration monitor of claim 29 defined further to include:
- a protective cover for covering a portion of the exposed lead portions of the receiving light conductor and for substantially preventing the exposed lead portions of the receiving light conductor and the sending light conductor from becoming entangled about the individual.

31. The respiration monitor of claim 23 defined further to include:
- a protective cover for covering a portion of the sending light conductor extending from the detector housing for substantially preventing the sending light conductor from becoming entangled about the individual; and
- a protective cover for covering a portion of the receiving light conductor extending from the detector housing for substantially preventing the receiving light conductor from becoming entangled about the individual.

32. The respiration monitor of claim 24 wherein the means for receiving light from the sending end of the receiving light conductor is defined further to include:
- means for receiving light from the sending end of the receiving light conductor and providing an output electrical analog signal indicative of the intensity of light receiving from the receiving light conductor; and
- means for receiving the electrical analog signal indicative of the intensity of the light received from the receiving light conductor and for providing an output alarm signal in response to substantially no change in the received electrical analog signal for a predetermined period of time.

33. The respiration monitor of claim 32 defined further to include:
- alarm means receiving the alarm signal and providing a perceivable output indication in response to receiving the alarm signal.

34. The respiration monitor of claim 23 wherein the means for receiving light from the sending end of the receiving light conductor and determining indication of respiration motion is defined further to include:
- means for converting the light received from the sending end of the receiving light conductor to a digital signal indicative of the intensity of the light received from the sending end of the receiving light conductor; and
- means for receiving the digital signal indicative of changes in the intensity of the light received from the sending end of the receiving light conductor and providing an output alarm signal in response to determining no change in the state of the received digital signal for a predetermined period of time thereby indicating an absence of respiration motion for the predetermined period of time.

35. The respiration monitor of claim 34 wherein the means for receiving light from the sending end of the receiving light conductor and determining indication of respiration motion is defined further to include:
- means for receiving the alarm signal indicative of an absence of respiration motion for the predetermined period of time and providing an audibly perceivable output indication indicating an absence of respiration motion for the predetermined period of time; and
- means for receiving the alarm signal indicative of absence of respiration motion for the predetermined period of time and providing a visually perceivable output indication indicative of an absence of respiration motion for the predetermined period of time.

36. The respiration monitor of claim 34 defined further to include:
- means for receiving the digital signal indicative of changes in the intensity of light received from the sending end of the receiving light conductor and determining the respiration rate of the individual being monitored.

37. The respiration monitor of claim 23 wherein the means for receiving light from the sending end of the receiving light conductor and determining indications of respiration motion is defined further to include:
- means for providing an operating power;
- means for determining the operating power is being provided and for determining the absence of providing the operating power supply, said means providing an output alarm signal in response to determining an absence of providing the operating power.

38. The respiration monitor of claim 37 wherein the means for providing operating power is defined further to include a line operating power supply and a battery operating power supply, and wherein the means for receiving light from the sending end of the receiving light conductor and determining indications of respiration motion is defined further to include:
- means for selectively switching to one of the battery operating power supply and to the line operating power supply for providing the operating power.

39. The respiration monitor of claim 23 wherein the receiving light conductor is disposed in the light opening in the detector housing and connected to the detector housing so that the receiving light conductor is not movable in the detector housing, and wherein the sending light conductor is movably disposed in the light opening in the detector housing, and wherein the strap assembly is defined further to include:
- a strap having opposite ends, the strap being constructed of a flexible, substantially non-elastic material; and
- an extension strip connected to one end of the strap and extending a distance therefrom, the extension strip being constructed of a flexible, elastic material expandable and contractable in response to respiration motion, the detector housing being connected to a portion of the strap and the sending light conductor being connectable to a portion of the extension strip so that respiration motion expands and contracts the extension strip thereby causing the sending light conductor to be moved in the light opening in a direction generally toward the receiving end of the receiving light conductor and in a direction generally a way from the receiving end of the receiving light conductor in response to respiration motion.

40. The respiration monitor of claim 23 wherein the strap assembly is defined further to include:

means for adjustably varying the length of the strap assembly.

41. The respiration monitor of claim 23 wherein the sending light conductor and the receiving light conductor each are defined further as being constructed of fiber optics.

42. A monitor for monitoring respiration motion, comprising:

a sending light conductor having a receiving end and a sending end, the sending light conductor being suitable for conducting light between the receiving and sending ends thereof;

a receiving light conductor having a receiving end and a sending end, the receiving light conductor being suitable for conducting light between the receiving and sending ends thereof;

means for positioning the sending end of the sending light conductor generally near and spaced a distance from the receiving end of the receiving light conductor, and for positioning the sending end of the sending light conductor and the receiving end of the receiving light conductor so the distance between the sending end of the sending light conductor and the receiving end of the receiving end of the receiving light conductor varies in response to motion to be monitored, said means comprising:

a detector housing having a light opening extending a distance therethrough, the sending end portion of the sending light conductor being insertable into the light opening and the receiving end of the receiving light conductor being insertable into the light opening with the sending light conductor and the receiving light conductor being positioned in the detector housing so the sending end of the receiving light conductor is spaced a distance from the receiving end of the receiving light conductor; and a light source for emitting light, the light source and being positioned near the receiving end of the sending light conductor and the sending light conductor receiving light from the light source and conducting such received light therethrough toward the sending end of the sending light conductor and the light being emitted from the sending end of the sending light conductor, the receiving end of the receiving light conductor receiving light from the sending end of the sending light conductor and conducting such received light therethrough toward the sending end of the receiving light conductor and the light being emitted from the sending end of the receiving light conductor, the intensity of the light received by the receiving end and emitted from the sending end of the receiving light conductor being indicative of the distance between the sending end of the sending light conductor and the receiving end of the receiving end of the receiving light conductor; and means for receiving light from the sending end of the receiving light conductor and determining indication of motion in response to changes in the intensity of the received light and providing an output indication indicative of motion.

43. The monitor of claim 42 wherein the light source is defined further as being adapted to emit infrared light, and wherein the detector housing is defined further to include a filter slot formed through a portion thereof, a portion of the filter slot intersecting the light opening in the detector housing, and wherein the means for positioning the sending and receiving light conductors is defined further to include:

an infrared filter disposed in the filter slot in the detector housing, the filter slot being positioned in the detector housing so the infrared filter is positioned generally between the sending end of the sending light conductor and the receiving end of the receiving light conductor and the infrared filter being adapted to pass substantially only infrared light.

44. The monitor of claim 43 wherein the receiving end portion of the receiving light conductor is defined further as being connected to the detector housing so that the receiving end portion of the receiving light conductor is not movable with respect to the detector housing, and wherein the sending end portion of the sending light conductor is defined further as being movable disposed in the light opening in the detector housing, the sending end portion of the sending light conductor being movable in the detector housing in response to motion, thereby increasing and decreasing the distance between the sending end of the sending light conductor and the receiving end of the receiving light conductor in response to motion.

45. The monitor of claim 42 wherein the receiving end portion of the receiving light conductor is defined further as being connected to the detector housing so that the receiving end portion of the receiving light conductor is not movable with respect to the detector housing, and wherein the sending end portion of the sending light conductor is defined further as being movable disposed in the light opening in the detector housing, the sending end portion of the sending light conductor being movable in the detector housing in response to motion.

46. The monitor of claim 42 wherein the means for receiving light from the sending end of the receiving light conductor and determining indications of motion is defined further to include:

means for providing an operating power;

means for determining the operating power is being provided and for determining the absence of providing the operating power supply, said means providing an output alarm signal in response to determining an absence of providing the operating power.

47. The monitor of claim 46 wherein the means for providing operating power is defined further to include a line operating power supply and a battery operating power supply, and wherein the means for receiving light from the sending end of the receiving light conductor and determining indications of motion is defined further to include:

means for selectively switching to one of the battery operating power supply and to the line operating power supply for providing the operating power.

48. The monitor of claim 42 wherein the sending light conductor and the receiving light conductor each are defined further as being constructed of fiber optics.

49. A monitor for monitoring motion comprising:

a sending light conductor having a receiving end and a sending end, the sending light conductor being suitable for conducting light between the receiving and sending ends thereof;

a receiving light conductor having a receiving end and a sending end, the receiving light conductor being suitable for conducting light between the receiving and sending end thereof;

light conductor support means, the sending end portion of the sending light conductor being affixed to the light conductor support means and the receiving end of the receiving light conductor being disposed on the light conductor support means, with the sending light conductor and the receiving light conductor being positioned so that the sending end of the sending light conductor is spaced a distance from and in alignment with the receiving end of the receiving light conductor said support means being constructed to maintain substantial linear alignment at all time, whereby the light passing therebetween will at all times define a substantially straight line; means for positioning the light conductor support means near the motion to be monitored whereby the distance between the sending end of the sending light conductor and the receiving end of the receiving light conductor is varied in response to the motion to be monitored;

a light source for emitting light, the light source being positioned near the receiving end of the sending light conductor and the sending light conductor receiving light from the light source and conducting such received light therethrough toward the sending end of the sending light conductor and the light being emitted from the sending end of the sending light conductor, the receiving end of the receiving light conductor receiving light from the sending end of the sending light conductor and conducting such received light therethrough toward the sending end of the receiving light conductor and the light being emitted from the sending end of the receiving light conductor, the intensity of the light received by the receiving end and emitted from the sending end of the receiving light conductor being indicative of the distance between the sending end of the sending light conductor and the receiving end of the receiving end of the receiving light conductor; and means for receiving light from the sending end of the receiving light conductor and determining indications of motion in response to changes in the intensity of the received light and providing an output indication indicative of motion.

50. The monitor of claim 49 wherein the means for receiving light from the sending end of the receiving light conductor and determining indications of motion is defined further to include:

means for providing an operating power;

means for determining the operating power is being provided and for determining the absence of providing the operating power supply, said means providing an output alarm signal in response to determining an absence of providing the operating power.

51. The monitor of claim 50 wherein the means for providing operating power is defined further to include a line operating power supply and a battery operating power supply, and wherein the means for receiving light from the sending end of the receiving light conductor and determining indications of motion is defined further to include:

means for selectively switching to one of the battery operating power supply and to the line operating power supply for providing the operating power.

52. The monitor of claim 49 wherein the sending light conductor and the receiving light conductor each are defined further as being constructed of fiber optics.

* * * * *